(12) United States Patent
Claude (10) Patent No.: US 7,364,748 B2
(45) Date of Patent: Apr. 29, 2008

(54) CONTROLLED MORPHOLOGIES IN POLYMER DRUG FOR RELEASE OF DRUGS FROM POLYMER FILMS

(75) Inventor: Charles David Claude, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 524 days.

(21) Appl. No.: 10/817,570

(22) Filed: Apr. 1, 2004

(65) Prior Publication Data

US 2004/0191293 A1   Sep. 30, 2004

Related U.S. Application Data

(63) Continuation of application No. 09/822,952, filed on Mar. 30, 2001, now Pat. No. 6,780,424.

(51) Int. Cl.
*A61F 13/00* (2006.01)
*A61F 2/00* (2006.01)

(52) U.S. Cl. .................. 424/422; 424/423; 424/424

(58) Field of Classification Search ............... 424/422
See application file for complete search history.

(56) References Cited

U.S. PATENT DOCUMENTS

| | | | |
|---|---|---|---|
| 2,072,303 A | 3/1937 | Herrmann et al. | ....... 128/335.5 |
| 2,386,454 A | 10/1945 | Frosch et al. | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,329,383 A | 5/1982 | Joh | |
| 4,343,931 A | 8/1982 | Barrows | |
| 4,529,792 A | 7/1985 | Barrows | |
| 4,611,051 A | 9/1986 | Hayes et al. | |
| 4,656,242 A | 4/1987 | Swan et al. | |
| 4,733,665 A | 3/1988 | Palmaz | |
| 4,800,882 A | 1/1989 | Gianturco | |
| 4,882,168 A | 11/1989 | Casey et al. | ............... 424/468 |
| 4,886,062 A | 12/1989 | Wiktor | |
| 4,931,287 A | 6/1990 | Bae et al. | |
| 4,941,870 A | 7/1990 | Okada et al. | |
| 4,977,901 A | 12/1990 | Ofstead | ...................... 128/772 |

(Continued)

FOREIGN PATENT DOCUMENTS

DE   42 24 401   1/1994

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Shelley A. Dodson
*Assistant Examiner*—Konata M. George
(74) *Attorney, Agent, or Firm*—Squire Sanders & Dempsey, LLP (57) ABSTRACT

The present invention includes a drug release system. The drug release system comprises a bulk polymer phase and a polymeric drug-enriched phase within the bulk polymer phase. At least one drug is incorporated into the drug-enriched phase.

9 Claims, 1 Drawing Sheet

U.S. PATENT DOCUMENTS

| | | | |
|---|---|---|---|
| 5,019,096 A | 5/1991 | Fox, Jr. et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,219,980 A | 6/1993 | Swidler | |
| 5,258,020 A | 11/1993 | Froix | |
| 5,272,012 A | 12/1993 | Opolski | |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | |
| 5,328,471 A | 7/1994 | Slepian | 604/101 |
| 5,330,768 A | 7/1994 | Park et al. | 424/501 |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | 525/54.1 |
| 5,464,650 A | 11/1995 | Berg et al. | |
| 5,485,496 A | 1/1996 | Lee et al. | |
| 5,516,881 A | 5/1996 | Lee et al. | |
| 5,569,463 A | 10/1996 | Helmus et al. | |
| 5,578,073 A | 11/1996 | Haimovich et al. | 623/1 |
| 5,584,877 A | 12/1996 | Miyake et al. | |
| 5,605,696 A | 2/1997 | Eury et al. | 424/423 |
| 5,607,467 A | 3/1997 | Froix | |
| 5,609,629 A | 3/1997 | Fearnot et al. | |
| 5,610,241 A * | 3/1997 | Lee et al. | 525/411 |
| 5,616,338 A | 4/1997 | Fox, Jr. et al. | |
| 5,624,411 A | 4/1997 | Tuch | |
| 5,628,730 A | 5/1997 | Shapland et al. | 604/21 |
| 5,644,020 A | 7/1997 | Timmermann et al. | |
| 5,649,977 A | 7/1997 | Campbell | |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | |
| 5,679,400 A | 10/1997 | Tuch | |
| 5,700,286 A | 12/1997 | Tartaglia et al. | 623/1 |
| 5,702,754 A | 12/1997 | Zhong | |
| 5,711,958 A | 1/1998 | Cohn et al. | |
| 5,716,981 A | 2/1998 | Hunter et al. | 514/449 |
| 5,721,131 A | 2/1998 | Rudolph et al. | |
| 5,723,219 A | 3/1998 | Kolluri et al. | |
| 5,735,897 A | 4/1998 | Buirge | |
| 5,746,998 A | 5/1998 | Torchilin et al. | 424/9.4 |
| 5,759,205 A | 6/1998 | Valentini | |
| 5,776,184 A | 7/1998 | Tuch | |
| 5,783,657 A | 7/1998 | Pavlin et al. | |
| 5,788,979 A | 8/1998 | Alt et al. | |
| 5,800,392 A | 9/1998 | Racchini | 604/96 |
| 5,820,917 A | 10/1998 | Tuch | |
| 5,824,048 A | 10/1998 | Tuch | |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | |
| 5,837,313 A | 11/1998 | Ding et al. | 427/2.21 |
| 5,849,859 A | 12/1998 | Acemoglu | |
| 5,851,508 A | 12/1998 | Greff et al. | 424/9.411 |
| 5,854,376 A | 12/1998 | Higashi | |
| 5,858,746 A | 1/1999 | Hubbell et al. | |
| 5,865,814 A | 2/1999 | Tuch | 604/265 |
| 5,869,127 A | 2/1999 | Zhong | |
| 5,873,904 A | 2/1999 | Ragheb et al. | 623/1 |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | 525/523 |
| 5,932,299 A | 8/1999 | Katoot | |
| 5,955,509 A | 9/1999 | Webber et al. | 514/772.7 |
| 5,958,385 A | 9/1999 | Tondeur et al. | |
| 5,962,138 A | 10/1999 | Kolluri et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | |
| 6,001,382 A | 12/1999 | Levy | 424/405 |
| 6,010,530 A | 1/2000 | Goicoechea | 623/1 |
| 6,011,125 A | 1/2000 | Lohmeijer et al. | |
| 6,015,541 A | 1/2000 | Greff et al. | 424/1.25 |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | 514/781 |
| 6,080,488 A | 6/2000 | Hostettler et al. | |
| 6,096,070 A | 8/2000 | Ragheb et al. | 623/1 |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | 427/2.3 |
| 6,159,978 A | 12/2000 | Myers et al. | |
| 6,165,212 A | 12/2000 | Dereume et al. | 623/1.13 |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,381 B1 | 4/2002 | Hossainy et al. | |

| | | |
|---|---|---|
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossaony et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,780,424 B2 * | 8/2004 | Claude .................. 424/423 |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |

| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | 0 301 856 | 2/1989 |
| SU | 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/17577 | 3/2001 |
| WO | WP 01/15751 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/documents?reg=1061848017752, printed Aug. 25, 2003 (2 pages).

Barbucci et al., *Coating of commercially available materials with a new heparinizable material*, J. Biomed. Mater. Res. 25:1259-1274 (Oct. 1991).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Nordrehaug et al., *A novel biocompatible coating applied to coronary stents*, EPO Heart Journal 14, p. 321 (P1694), Abstr. Suppl. (1993).

Ozaki et al., *New Stent Technologies*, Progress in Cardiovascular Diseases, vol. XXXIX(2):129-140 (Sep./Oct. 1996).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Chung et al., *Inner core segment design for drug delivery control of thermo-responsive polymeric micelles*, Journal of Controlled Release 65:93-103 (2000).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Ohsawa et al., *Preventive Effects of an Antiallergic Drug, Permirolast Potassium, on Restenosis After Percutaneous Transluminal Coronary Angioplasty*, American Heart Journal 136(6):1081-1087 (Dec. 1998).

Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).

Shigeno, *Prevention of Cerebrovascular Spasm By Bosentan, Novel Endothelin Receptor*; Chemical Abstract 125:212307 (1996).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

CONTROLLED MORPHOLOGIES IN POLYMER DRUG FOR RELEASE OF DRUGS FROM POLYMER FILMS

CROSS REFERENCE

This application is a continuation of patent application Ser. No. 09/822,952 filed Mar. 30, 2001 now U.S. Pat. No. 6,780,424.

BACKGROUND OF THE INVENTION

The present invention relates to a system for controlled drug release within a vessel lumen, and to a method and to a device for controlled drug release.

A device for providing a continuous release of drugs over an extended period of time following from a single administration of a drug releasing material has wide application in treating disease. One type of continuous drug release mechanism is based upon degradation of biodegradable polymers. The biodegradable polymers have drugs incorporated within them. As the biodegradable polymers hydrolyze over time, the drugs are released. Hydroxycarboxylic acid polymers have been used to release drugs in this manner.

One other modality of drug release is a prolonged, though discontinuous release of drugs. Frequently, with a discontinuous release, there is a lag phase of no or negligible drug release when a drug delivery device is delivered to an in situ site for drug release.

One problem with sustaining drug release is that when drugs, particularly water soluble drugs, are incorporated into polymers, it is difficult to prevent a rapid, uncontrolled release of the drugs. As used herein, the term "water soluble drug" is defined as a hydrophilic compound with a solubility in water greater than 1 percent (w/v) and that is practically insoluble in nonpolar organic solvents such as ethyl acetate, methylene chloride, chloroform, toluene, or hydrocarbons. This rapid, uncontrolled release from a drug-polymeric matrix is known as a "burst effect." The burst effect is particularly troublesome with high drug loading.

One other type of uncontrolled drug release is characterized by a "lag effect." The lag effect occurs when the rate of drug release decreases to a negligible value.

The degree of drug release from a polymeric-drug matrix is, in part, controlled by the morphology of the polymeric-drug matrix. The morphology is, for some embodiments, a single-phase dispersion and for other embodiments, is a multi-phase dispersion. A single-phase dispersion is typically transparent when viewed in natural light. The single phase dispersion is clear and transparent because both the drug and the polymer have a mutual miscibility. A multi-phase dispersion has micro domains that give the dispersion a cloudy appearance. For some multi-phase dispersions, drugs are embedded in a polymeric matrix as particles.

Drug release is also controlled by the degree of drug loading. Matrices that have dispersed drug particles that do not contact each other tend to have a slow release of drug. A drug carrier such as blood is typically required to move the drug through the matrix and into the bloodstream of a living being.

Drug-polymeric matrices have been used to deliver drugs in situ through a vehicle such as a stent. The drug-polymeric matrix has been applied as a coating or a wrap to the stent. U.S. Pat. No. 5,605,696, which issued Feb. 25, 1997, describes a drug loaded polymeric material that is applied to an intravascular stent. The drug-polymeric matrix defines pores, multilayered to permit a combination of different drugs in a single stent. The stent also includes a rate controlling membrane that controlled retention and delivery of selected drugs to the affected blood vessel. The drug is dispersed as small particles, having a maximum cross-sectional dimension of 10 microns.

SUMMARY OF THE INVENTION

One embodiment of the present invention includes a drug release system. The drug release system releases one or more drugs when implanted in a human being or other vertebrate but does not display a substantial release of drugs when outside of the human being or other vertebrates. The drug release system comprises a bulk polymer phase and a polymeric drug-enriched phase within the bulk polymer phase. The drug release system also includes at least one drug that is incorporated in the polymeric drug-enriched phase. The drug release system of the present invention releases one or more drugs in situ while decreasing the rate of release of the drug when the device is not in situ. The drug profile release is predictable and preselectable.

Another embodiment of the present invention includes a coating that comprises a drug release system. The drug release system has desirable film properties which render it useful as a coating for an implantable device. The present invention also includes an implantable device with a coating that is adhered to the implantable device. The coated implantable device releases one or more drugs in a predictable and preselectable manner when implanted in a human being or other vertebrate.

Another embodiment of the present invention includes a method for substantially continuously releasing drugs. The method includes attaching or adhering a drug delivery system to an implantable medical device. The drug delivery system comprises a bulk polymer phase and a polymeric drug-enriched phase within the bulk polymer phase. The drug release system also includes one or more drugs that are incorporated in the polymeric drug-enriched phase.

One other embodiment includes a device for continuously and predictably releasing drugs. The device comprises a drug release system that comprises a bulk polymer phase. The drug release system also includes a drug-enriched polymeric phase within the bulk polymer phase. The drug release system also includes at least one drug which is incorporated into the polymeric drug-enriched phase wherein the drug-enriched phase comprises sites within the bulk polymer phase that are continuous in both cross-section and longitudinal directions. Other embodiments of the device include implantable devices, such as a stent, catheter or guidewire, to which the drug release system is attached or adhered.

Another embodiment of the present invention includes a method for making a device for a continuous release of drugs. The method comprises providing a bulk phase polymer and providing a drug that is substantially insoluble in the bulk phase polymer. The method also includes providing a drug enriched polymer. The drug enriched polymer is substantially insoluble in the bulk polymer. One or more of the drugs are soluble in the drug-enriched polymer. The method further comprises providing a solvent. The bulk phase polymer, the drug enriched polymer and the drug or drugs are blended in the solvent so that the drug or drugs are incorporated into the drug receiving polymer and the drug enriched polymer is dispersed within the bulk polymer.

DETAILED DESCRIPTION

One embodiment of the present invention includes a drug release system comprising two or more polymers that are insoluble in each other. The polymers are blended in a solvent to form two polymer phases which create a polymer blend. At least one drug is added to the polymer blend. The drug or drugs are soluble in one of the polymer phases, hereinafter referred to as the "drug-enriched polymer" or "drug enriched polymer phase." The polymer blend with the drug enriched polymer phase is removed from the solvent and is allowed to set. Once set, this drug release system has a morphology that has a predictable and preselectable drug release profile with desirable film properties. The desirable film properties include adherence or attachment to a polymeric or metal surface of an implantable device. Thus, the drug release system serves a dual function of predictable, preselectable drug delivery and coating an implantable device.

The term "preselectable" as used herein refers to an ability to preselect one or more drugs to be released. "Preselectable," for some embodiments, also refers to a rate of drug release.

The polymer phase that includes the soluble drug, the drug-enriched polymer phase, preferably has a glass transition temperature, Tg, less than human body temperature of about 37 degrees Centigrade. This polymer phase shall be referred to herein as a "drug-enriched polymer." Upon incorporating one or more drugs into the polymer, the polymer is kept at a temperature that is lower than the glass transition temperature. The term "glass transition temperature" as used herein refers to a temperature at which the polymer chain undergoes long range motion characterized by a transition from a glassy state to a rubbery state. The glass transition temperature is also the temperature at which the rate of diffusion within the polymer phase changes by several orders of magnitude as the polymer goes from the glassy state to the rubbery state.

A polymer with a Tg that is less than 37 degrees Centigrade is used as the drug-enriched polymer because the diffusion rate of molecules, such as drug molecules within the polymer, decreases one to two orders of magnitude when the polymer is exposed to a temperature that is below the Tg. The Tg features of the drug enriched polymer impart to the polymer features that allow additional control of the drug delivery rate. For instance, when the polymer is at a temperature below its Tg, it will not be within a living being, such as a human being. At these lower temperatures, the drug diffusion is suppressed and the drug does not prematurely diffuse through the bulk polymer. This is desirable because outside of a human being, drug diffusion through the polymer is problematic. Once the drug-enriched polymer phase is implanted, the temperature of the polymer approaches its Tg and the rate of diffusion of drug through the polymer increases. The drug or drugs are deliverable to a predetermined site, such as to a lesion in a blood vessel. Once at this site, the drugs diffuse through the drug-enriched polymer. Polymers which can be used as the drug enriched phase include polyethylene oxide, PEO, and poly n-vinyl pyrrolidone.

The drug enriched polymer is at a concentration greater than the percolation threshold concentration, which is about 33-36%, assuming a morphology of spherical domains, to form a continuous drug enriched phase within the bulk polymer film. The term "percolation threshold" as is used herein refers to a state achieved when an aqueous drug enriched phase forms a continuous, interconnecting network throughout the bulk polymer thickness. The continuous drug enriched phase is one where the drug-enriched polymer phase is substantially uniformly distributed within the bulk phase, such as is shown generally, in one perspective view, at 10, in FIG. 1.

Figure 1:
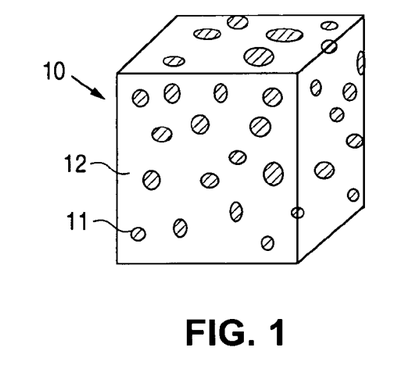
FIG. 1 is a perspective view of one embodiment of the drug delivery system of the present invention wherein a system component is below the percolation threshold.

The continuous drug-enriched polymer phase, is illustrated at 11 in FIG. 1, for one embodiment. The bulk polymer 12 forming the phase which is not drug-enriched, referred to herein as the "bulk phase" or "bulk matrix" has acceptable film properties. One suitable polymer for use in the drug release system, as a bulk phase polymer, is poly (ethylene-co-vinyl) alcohol, which is also known as EVAL. EVAL is a thermoplastic polymer, manufactured by EVAL Company of America (EVALCA), of Lisle, Ill. This polymer 12 has a formulation which is the following:

The drug-enriched polymer containing the drug has, for one embodiment, the formula:

One drug delivery system is composed of two components: one, a hydrophobic component, including but not limited to poly(ethylene-co-vinyl alcohol), and two, a hydrophilic component, which includes but is not limited to polyethylene glycol. The dissimilarity of solubility parameters of the components results in a phase separation of the two polymer phases. The two polymers are blended in a common solvent, such as dimethyl sulfoxide or N,N-dimethylacetamide, to form a solution. At least one therapeutic drug is added to the solution, such as the therapeutic drug, actinomycin D. However, the therapeutic drug or drugs are not limited to the antiproliferative class of drugs which has preferential solubility in the hydrophilic phase.

For some embodiments, the drug delivery system comprising the drug and polymer solution is applied to an implantable device to form a coating on the device. The coated device is dried to remove the solvent, by vacuum or by convection processing. The drying allows the polymers within the applied solution to form phases and to separate. Once dried, the coating retains flexibility.

If the volume percent of the drug enriched hydrophilic phase is less than about 30%, the hydrophilic polymer and drug will exhibit a discontinuous pore structure, as shown at 10 in FIG. 1. The discontinuous pore structure shown in FIG. 1 is defined as being below the percolation threshold.

Figure 2:
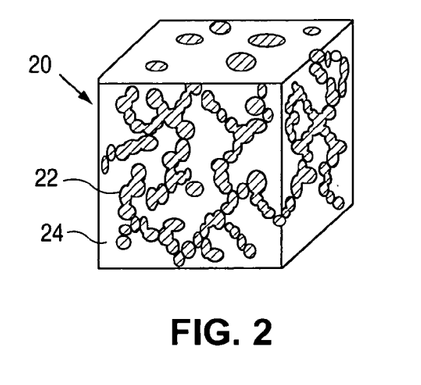
FIG. 2 is a perspective view of one embodiment of the drug delivery system of the present invention wherein a system component is above the percolation threshold.

If the volume percent of the drug enriched hydrophilic phase is greater than about 30%, the hydrophilic polymer and drug will exhibit a pore structure 22 that is continuous throughout the volume of the bulk polymer 24, as shown generally at 20 in FIG. 2. The continuous pore structure 22 within the bulk polymer volume of the polymer 24 is defined as being above the percolation threshold.

The elution of the drug from a drug release coating, such as is shown in FIG. 1, below the percolation threshold, is dependent upon the diffusion of the drug within the drug-enriched polymer 11 through the hydrophobic bulk polymer 12. This is contrary to the diffusion of the drug from a drug release coating above the percolation threshold, such as is illustrated in FIG. 2, which is dependent upon the diffusion of the drug from the pore network 22, and upon the mean pore length.

Common solvents and co-solvents usable for the blending of the polymers include dimethyl sulfoxide, N,N-dimethylacetamide, dimethyl sulfoxide-tetrahydrofuran, and isopropanol-water.

Once the polymers are blended and the drug is incorporated in the drug-enriched polymer, the solvent is evaporated. The evaporation is carried out, for some embodiments, at a reduced pressure and at a temperature that is as close to ambient temperature as possible.

Examples of such drugs include antiproliferative substances as well as antineoplastic, anti-inflammatory antiplatelet, anticoagulant, antifigrin, antithrombin, antimitotic, antibiotic, antioxidant, and combinations thereof. A suitable example of an antiproliferative substance includes actinomycin D, or derivatives and analogs thereof, manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I1, actinomycin X1, and actinomycin C1. Examples of suitable antineoplastics include paclitaxel and docetaxel. Examples of suitable antiplatelets, anticoagulants, antifibrins, and antithrombins, include sodium heparin, low molecular weight heparin, hirudin, argatroban, forskolin, vapisprost, prostacyclin and prostacyclin analogs, dextran, D-phe-pro-arg-chloromethylketone (synthetic antithrombin), dipyridamole, glycoprotein lib/IIIa platelet membrane receptor antagonist, recombinant hirudin, thrombin inhibitor, available from Biogen, and 7E-3B, an antiplatelet drug from Centocore. Examples of suitable antimitotic agents include methotrexate, azathioprine, vincristine, vinblastine, antiproliferative agents include angiopeptin (a somatostatin analog from Ibsen), angiotensin converting enzyme inhibitors such as CAPTOPRIL, available from Squibb, CILAZAPRIL, available form Hoffinan-LaRoche, or LISINOPRIL, available form Merck, calcium channel blockers such as Nifedipine, colchicine, fibroblast growth factor (FGF) antagonists, fish oil, omega 3-fatty acid, histamine antagonists, LOVASTATIN, an inhibitor of AMG-CoA reductase, a cholesterol lowering drug from Merck, a cholesterol lowering drug, monoclonal antibodies such as PDGF receptors, nitroprusside, phosphodies terase, inhibitors, prostaglandin inhibitor, Seramin, a PDGF antagonist, serotonin blockers, steroids, thioprotease inhibitors, triazolopyrimidine, a PDGF antagonist, and nitric oxide. Other therapeutic substances or agents which may be appropriate include alpha-interferon, genetically engineered epithelial cells, and dexamethasone.

Figure 3A:
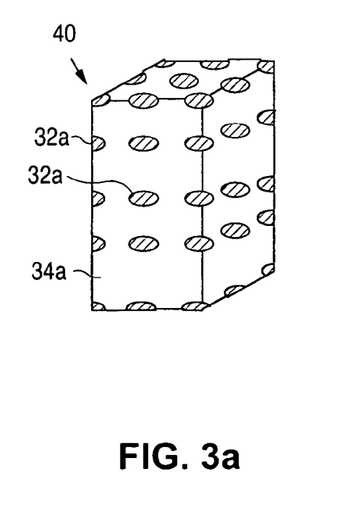
FIG. 3a is a perspective view of the drug delivery system of the present invention wherein the pore structure is discontinuous.

In another embodiment, the drug delivery system comprises a polymer film doped with one or more therapeutic drugs. The polymer film is comprised of a graft copolymer, the copolymer having segments that differ significantly in their solubility parameters. The solubility differences result in phase separation of the two segments. In this embodiment, the hydrophobic polymer is poly(ethylene-co-vinyl alcohol), commercially known as EVAL. In the embodiment, a hydrophilic copolymer such as a polyethylene oxide with a molecular weight between 3200 and 20,000 with an isocyanate functionality is grafted as a side chain, in the following chemical reaction:

in which one or more drugs is incorporated. At higher concentrations, the drug enriched polymer phase coalesces to form a lamellar morphology. The drug release embodiment 40a, shown in FIG. 3a, is a discontinuous pore structure, with the drug-enriched polymer phase 32a discretely dispersed in the bulk phase 34a.

Figure 3B:
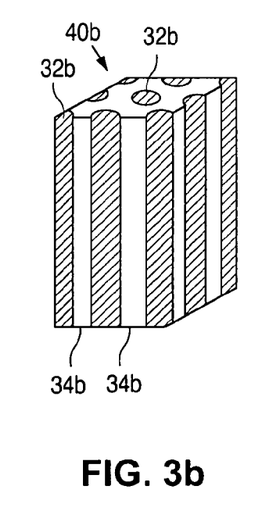
FIG. 3b is a perspective view of the drug delivery system of the present invention wherein the pore structure is semi-continuous.
Figure 3C:
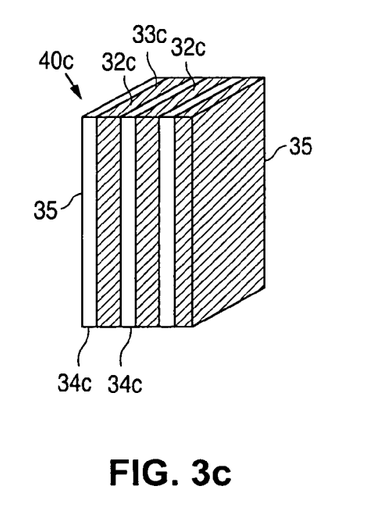
FIG. 3c is a perspective view of another embodiment of the drug delivery system of the present invention wherein the pore structure is continuous.

The drug-enriched polymer structure 32b in FIG. 3b has a semi-continuous phase and in FIG. 3c, the drug-enriched polymer 32c has a continuous phase in which the drug is soluble and diffusible from the continuous phase, when implanted into a living being. The semi-continuous phase 32b comprises sites that are discrete in cross-section but continuous in a longitudinal direction, as is shown in FIG. 3b. The continuous phase 32c, shown in FIG. 3c, defines a channel 33c in which the drug is diffusible from the bulk polymer 34c to the polymer interface 35. The drug-enriched sites are continuous in both cross-section and in a longitudinal direction.

EXAMPLE 1

On exemplary composition that produces the drug release morphology of FIG. 3c includes an EVAL polymer with 56 weight percent ethylene groups, 43.32 weigh percent vinyl alcohol functionalities and 0.68 weight percent vinyl ether groups. The weight percent refers to the percent of the total The graft copolymer with a molecular weight of 3200 daltons is functionalized with 0.27 mol percent of the hydroxyl functionalities of the poly(ethylene-co-vinyl alcohol) and has an average of two ethylene oxide polymers grafted to the polymer. The total volume fraction of hydrophilic polymer and drug occupies approximately 35% of the polymer matrix and assumes a cylindrical-like pore morphology. The grafted co-polymer with a molecular weight of 3200 daltons functionalized with 0.68 mole percent of the hydroxyl functionalities has an average of five co-polymer segments attached to any given polymer chain. The hydrophilic graft polymer volume containing the polyethylene oxide functionality and the drug, forming a drug enriched polymer, are present at approximately 50 volume percent. The drug enriched polymer assumes a lamellar structure as is shown at 40c in FIG. 3c.

The morphologies of the drug enriched graft polymer 32 within the bulk polymer substrate 34, are shown at 40a, 40b and 40c, respectively, in FIGS. 3a, 3b and 3c. These different morphologies are due to an increasing concentration of the drug enriched polymer phase 32a, 32b and 32c, respectively, drug release system weight. The vinyl ether groups are functionalized with PEO-isocyanate, which forms a urethane linkage, using groups that have a molecular weight of a side group of 3200 g/mol. The side groups comprise 33 weight percent of the total EVAL/PEO polymer. The composition of the PEO-isocyanate blend is 75 weight percent functionalized EVAL and 25 weight percent drug. This composition gives rise to a 50 weight percent hard, bulk pause and a 50 percent drug/PEO side chain phase. The final structure is a lamellar structure.

The chemical reaction is as follows:

-continued (x)=66 weight %; (y)=44 weight %. M is approximately equal to 70 units. Molecular weight is approximately 3200 units. With the drug release system such as is shown at 40c in FIG. 3c, drug release is substantially continuous within a human being.

The drug release system of the present invention is deliverable to a treatment site by attachment to a device such as a stent or catheter or guidewire. For other embodiments, the drug release system is encapsulated and ingested or subcutaneously injected. For other embodiments, the drug release system is adhered to a prosthetic device or a graft or other implantable device by methods known to those skilled in the art.

Once positioned within a living being by one of the implantable devices, the drug release system commences delivering drugs because the polymer component of the drug-laden phase is at a temperature below its glass transition temperature. The release of drugs is substantially continuous.

While specified embodiments of the invention have been herein described, it is to be appreciated that various changes, rearrangements and modifications may be made therein without departing from the scope of the invention as defined by the appended claims.

What is claimed is:

1. An implantable medical device comprising a coating and a therapeutic substance, the coating including a graft polymer having a main chain segment and a side chain segment, wherein the main chain segment has a different degree of solubility than the side chain segment so as to cause phase separation of the segments on the coating on the device and wherein the therapeutic substance has a preferential solubility for one segment over the other segment, wherein the main chain segment includes poly(ethylene-co-vinyl alcohol) and the side chain segment includes poly(ethylene oxide).

2. The implantable medical device of claim 1, wherein the side chain segment is derived from polyethylene oxide having an isocyanate moiety.

3. An implantable medical device comprising a coating, the coating including a poly(ethylene-co-vinyl alcohol) conjugated to a polyethylene oxide.

4. The implantable device of claim 3, additionally comprising a drug.

5. The implantable device of claim 3, additionally comprising a drug having preferential solubility for the polyethylene oxide.

6. An implantable medical device comprising a coating, the coating including a product of reaction of poly(ethylene-co-vinyl alcohol) and a polyethylene oxide having an isocyanate functionality.

7. The implantable medical device of claim 1 which is a stent.

8. The implantable medical device of claim 3 which is a stent.

9. The implantable medical device of claim 6 which is a stent.

* * * * *